United States Patent
Kohring et al.

(10) Patent No.: US 11,571,532 B2
(45) Date of Patent: Feb. 7, 2023

(54) INTRANASAL DEVICE WITH DIP TUBE

(71) Applicant: Impel Pharmaceuticals Inc., Seattle, WA (US)

(72) Inventors: Craig Frederick Kohring, Seattle, WA (US); Christopher William Fuller, Seattle, WA (US)

(73) Assignee: Impel Pharmaceuticals Inc., Seattle, WA (US)

( * ) Notice: Subject to any disclaimer, the term of this patent is extended or adjusted under 35 U.S.C. 154(b) by 960 days.

(21) Appl. No.: 16/198,403

(22) Filed: Nov. 21, 2018

(65) Prior Publication Data

US 2019/0151579 A1    May 23, 2019

Related U.S. Application Data

(60) Provisional application No. 62/589,306, filed on Nov. 21, 2017.

(51) Int. Cl.
*A61M 15/08* (2006.01)
*A61M 15/00* (2006.01)
(Continued)

(52) U.S. Cl.
CPC ............ *A61M 15/08* (2013.01); *A61M 11/02* (2013.01); *A61M 15/0021* (2014.02);
(Continued)

(58) Field of Classification Search
CPC .. A61M 15/08; A61M 11/02; A61M 15/0021; A61M 15/0036; A61M 15/0035;
(Continued)

(56) References Cited

U.S. PATENT DOCUMENTS 2,933,259 A    4/1960  Raskin
3,425,414 A    2/1969  Roche
(Continued)

FOREIGN PATENT DOCUMENTS

DE         19518580 A1   11/1996
DE    102013100473 A1    7/2014
(Continued)

OTHER PUBLICATIONS

Appasaheb, et al., "Review on Intranasal Drug Delivery System", Journal of Advanced Pharmacy Education and Research, vol. 3, Issue 4, Oct. 2013, 14 pages.
(Continued)

*Primary Examiner* — Victoria Murphy
(74) *Attorney, Agent, or Firm* — Fenwick & West LLP

(57) ABSTRACT

A device for delivering a compound to the olfactory region of the nasal cavity includes an actuator body and a tip configured to removably couple to the actuator body. The actuator body comprises a propellant channel in fluid communication with a propellant canister. The tip comprises a tip stem, a dip tube, a delivery channel, one or more puncture members, and an outlet orifice. The tip stem receives a compound container containing the compound and the compound container moves between a sealed state and an unsealed state. The one or more puncture members are each configured to puncture the compound container when the compound container is in the unsealed state. Propellant released from the canister travels through the propellant channel and into the punctured compound container, thereby contacting the compound and propelling the compound through the delivery channel and out the outlet orifice.

16 Claims, 8 Drawing Sheets

(51) Int. Cl.
*A61M 11/02* (2006.01)
*B05B 11/00* (2006.01)
*B05B 1/00* (2006.01)

(52) U.S. Cl.
CPC .... *A61M 15/0035* (2014.02); *A61M 15/0036* (2014.02); *B05B 1/00* (2013.01); *B05B 11/00* (2013.01); *A61M 15/009* (2013.01); *A61M 15/0028* (2013.01); *A61M 2205/582* (2013.01)

(58) Field of Classification Search
CPC ............ A61M 15/0028; A61M 15/009; A61M 2205/582; A61M 15/003; A61M 15/0086; B05B 11/00; B05B 1/00; B05B 9/0838; B05B 9/0833
See application file for complete search history.

(56) References Cited

U.S. PATENT DOCUMENTS

| | | |
|---|---|---|
| 3,888,253 A | 6/1975 | Watt et al. |
| 3,906,950 A | 9/1975 | Cocozza |
| 3,908,654 A | 9/1975 | Lhoest et al. |
| 3,971,377 A | 7/1976 | Damani |
| 4,095,596 A | 6/1978 | Grayson |
| 4,187,985 A | 2/1980 | Goth |
| 4,227,522 A | 10/1980 | Carris |
| 4,353,365 A | 10/1982 | Hallworth et al. |
| 4,412,573 A | 11/1983 | Zdeb |
| 4,620,670 A | 11/1986 | Hughes |
| 4,702,415 A | 10/1987 | Hughes |
| 4,896,832 A | 1/1990 | Howlett |
| 4,995,385 A | 2/1991 | Valentini et al. |
| 5,224,471 A | 7/1993 | Marelli et al. |
| 5,307,953 A | 5/1994 | Regan |
| 5,331,954 A | 7/1994 | Rex et al. |
| 5,349,947 A | 9/1994 | Newhouse et al. |
| 5,382,236 A | 1/1995 | Otto et al. |
| 5,398,850 A | 3/1995 | Sancoff et al. |
| 5,435,282 A | 7/1995 | Haber et al. |
| 5,505,193 A | 4/1996 | Ballini et al. |
| 5,516,006 A | 5/1996 | Meshberg |
| 5,711,488 A | 1/1998 | Lund |
| 5,715,811 A | 2/1998 | Ohki et al. |
| 5,797,390 A | 8/1998 | McSoley |
| 5,814,020 A | 9/1998 | Gross |
| 5,819,730 A | 10/1998 | Stone et al. |
| 5,823,183 A | 10/1998 | Casper et al. |
| 5,881,719 A | 3/1999 | Gottenauer et al. |
| 5,901,703 A | 5/1999 | Ohki et al. |
| 5,906,198 A | 5/1999 | Flickinger |
| 5,910,301 A | 6/1999 | Farr et al. |
| 5,954,696 A | 9/1999 | Ryan |
| 6,062,213 A | 5/2000 | Fuisz et al. |
| 6,079,634 A | 6/2000 | Noakes et al. |
| 6,092,522 A | 7/2000 | Calvert et al. |
| 6,145,703 A | 11/2000 | Opperman |
| 6,158,676 A | 12/2000 | Hughes |
| 6,180,603 B1 | 1/2001 | Frey |
| 6,186,141 B1 | 2/2001 | Pike et al. |
| 6,189,739 B1 | 2/2001 | von Schuckmann |
| 6,294,153 B1 | 9/2001 | Modi |
| 6,302,101 B1 | 10/2001 | Py |
| 6,313,093 B1 | 11/2001 | Frey |
| 6,347,789 B1 | 2/2002 | Rock |
| 6,367,471 B1 | 4/2002 | Genosar et al. |
| 6,367,473 B1 | 4/2002 | Käfer |
| 6,382,465 B1 | 5/2002 | Greiner Perth |
| 6,410,046 B1 | 6/2002 | Lerner |
| 6,491,940 B1 | 12/2002 | Levin |
| 6,540,983 B1 | 4/2003 | Adjei et al. |
| 6,569,463 B2 | 5/2003 | Patel et al. |
| 6,585,172 B2 | 7/2003 | Arghyris |
| 6,585,957 B1 | 7/2003 | Adjei et al. |
| 6,585,958 B1 | 7/2003 | Keller et al. |
| 6,595,202 B2 | 7/2003 | Gañán Calvo |
| 6,622,721 B2 | 9/2003 | Vedrine et al. |
| 6,644,305 B2 | 11/2003 | MacRae et al. |
| 6,644,309 B2 | 11/2003 | Casper et al. |
| 6,647,980 B1 | 11/2003 | Gizurarson |
| 6,681,767 B1 | 1/2004 | Patton et al. |
| 6,684,879 B1 | 2/2004 | Coffee et al. |
| 6,701,916 B2 | 3/2004 | Mezzoli |
| 6,715,485 B1 | 4/2004 | Djupesland |
| 6,734,162 B2 | 5/2004 | Van Antwerp et al. |
| 6,810,872 B1 | 11/2004 | Ohki et al. |
| 6,923,988 B2 | 8/2005 | Patel et al. |
| 7,033,598 B2 | 4/2006 | Lerner |
| 7,051,734 B2 | 5/2006 | Casper et al. |
| 7,163,013 B2 | 1/2007 | Harrison |
| 7,182,277 B2 | 2/2007 | Vedrine et al. |
| 7,200,432 B2 | 4/2007 | Lerner et al. |
| 7,214,209 B2 | 5/2007 | Mazzoni |
| 7,231,919 B2 | 6/2007 | Giroux |
| 7,258,119 B2 | 8/2007 | Mazzoni |
| 7,296,566 B2 | 11/2007 | Alchas |
| 7,347,201 B2 | 3/2008 | Djupesland |
| 7,377,901 B2 | 5/2008 | Djupesland et al. |
| 7,476,689 B2 | 1/2009 | Santus et al. |
| 7,481,218 B2 | 1/2009 | Djupesland |
| 7,543,581 B2 | 6/2009 | Djupesland |
| 7,655,619 B2 | 2/2010 | During et al. |
| 7,740,014 B2 | 6/2010 | Djupesland |
| 7,784,460 B2 | 8/2010 | Djupesland et al. |
| 7,799,337 B2 | 9/2010 | Levin |
| 7,832,394 B2 | 11/2010 | Schechter et al. |
| 7,841,337 B2 | 11/2010 | Djupesland |
| 7,841,338 B2 | 11/2010 | Dunne et al. |
| 7,854,227 B2 | 12/2010 | Djupesland |
| 7,866,316 B2 | 1/2011 | Giroux |
| 7,905,229 B2 | 3/2011 | Giroux et al. |
| 7,934,503 B2 | 5/2011 | Djupesland et al. |
| 7,975,690 B2 | 7/2011 | Djupesland |
| 7,994,197 B2 | 8/2011 | Cook et al. |
| 8,001,963 B2 | 8/2011 | Giroux |
| 8,047,202 B2 | 11/2011 | Djupesland |
| 8,119,639 B2 | 2/2012 | Cook et al. |
| 8,122,881 B2 | 2/2012 | Giroux |
| 8,146,589 B2 | 4/2012 | Djupesland |
| 8,171,929 B2 | 5/2012 | Djupesland et al. |
| 8,327,844 B2 | 12/2012 | Djupesland |
| 8,408,427 B2 | 4/2013 | Wong |
| 8,448,637 B2 | 5/2013 | Giroux |
| 8,511,303 B2 | 8/2013 | Djupesland |
| 8,517,026 B2 | 8/2013 | Amon |
| 8,522,778 B2 | 9/2013 | Djupesland |
| 8,550,073 B2 | 10/2013 | Djupesland |
| 8,555,877 B2 | 10/2013 | Djupesland |
| 8,555,878 B2 | 10/2013 | Djupesland |
| 8,596,278 B2 | 12/2013 | Djupesland |
| 8,733,342 B2 | 5/2014 | Giroux et al. |
| 8,757,146 B2 | 6/2014 | Hoekman et al. |
| 8,800,555 B2 | 8/2014 | Djupesland |
| 8,839,790 B2 | 9/2014 | Beck Arnon |
| 8,875,794 B2 | 11/2014 | Carlsen et al. |
| 8,899,229 B2 | 12/2014 | Djupesland et al. |
| 8,899,230 B2 | 12/2014 | Immel |
| 8,910,629 B2 | 12/2014 | Djupesland et al. |
| 8,925,544 B2 | 1/2015 | Flickinger |
| 8,978,647 B2 | 3/2015 | Djupesland et al. |
| 8,987,199 B2 | 3/2015 | Abdel Maksoud et al. |
| 9,010,325 B2 | 4/2015 | Djupesland et al. |
| 9,038,630 B2 | 5/2015 | Djupesland et al. |
| 9,067,034 B2 | 6/2015 | Djupesland et al. |
| 9,072,857 B2 | 7/2015 | Djupesland |
| 9,101,539 B2 | 8/2015 | Nagata et al. |
| 9,119,932 B2 | 9/2015 | Djupesland |
| 9,180,264 B2 | 11/2015 | Young et al. |
| 9,272,104 B2 | 3/2016 | Djupesland |
| 9,446,207 B2 | 9/2016 | Jung |
| 2002/0017294 A1 | 2/2002 | Py |
| 2002/0054856 A1 | 5/2002 | Jones |
| 2002/0092520 A1 | 7/2002 | Casper et al. |

(56) References Cited

U.S. PATENT DOCUMENTS

| | | | |
|---|---|---|---|
| 2002/0174864 A1* | 11/2002 | Alchas | B05B 11/02 128/200.14 |
| 2003/0017119 A1 | 1/2003 | Rabinowitz et al. | |
| 2003/0158527 A1 | 8/2003 | Mezzoli | |
| 2003/0217748 A1 | 11/2003 | Giroux | |
| 2004/0068222 A1 | 4/2004 | Brian | |
| 2004/0153033 A1* | 8/2004 | Mazzoni | A61M 15/0028 604/192 |
| 2004/0238574 A1 | 12/2004 | Merk et al. | |
| 2005/0000514 A1* | 1/2005 | Sullivan | A61M 15/0033 128/200.24 |
| 2005/0023376 A1 | 2/2005 | Anderson | |
| 2005/0028812 A1 | 2/2005 | Djupesland | |
| 2005/0036985 A1 | 2/2005 | Ensoli | |
| 2005/0098172 A1 | 5/2005 | Anderson | |
| 2005/0142072 A1 | 6/2005 | Birch et al. | |
| 2005/0274378 A1 | 12/2005 | Bonney et al. | |
| 2006/0107957 A1 | 5/2006 | Djupesland | |
| 2006/0219813 A1 | 10/2006 | Morrison | |
| 2006/0240092 A1 | 10/2006 | Breitenkamp et al. | |
| 2007/0056585 A1 | 3/2007 | Davies et al. | |
| 2007/0068514 A1 | 3/2007 | Giroux | |
| 2007/0074722 A1 | 4/2007 | Giroux et al. | |
| 2007/0119451 A1 | 5/2007 | Wang et al. | |
| 2007/0131224 A1 | 6/2007 | Giroux | |
| 2007/0172517 A1 | 7/2007 | Ben Sasson et al. | |
| 2007/0202051 A1 | 8/2007 | Schuschnig | |
| 2008/0054099 A1 | 3/2008 | Giroux et al. | |
| 2008/0163874 A1 | 7/2008 | Djupesland | |
| 2008/0178871 A1 | 7/2008 | Genova et al. | |
| 2008/0305077 A1 | 12/2008 | Frey et al. | |
| 2009/0320832 A1 | 12/2009 | Djupesland | |
| 2011/0053859 A1 | 3/2011 | Deadwyler et al. | |
| 2011/0057055 A1 | 3/2011 | Wong | |
| 2012/0195959 A1 | 8/2012 | Ishii | |
| 2014/0083424 A1 | 3/2014 | Haekman et al. | |
| 2014/0170220 A1 | 6/2014 | Cartt et al. | |
| 2014/0343494 A1 | 11/2014 | Hoekman et al. | |
| 2015/0057287 A1 | 2/2015 | Cook et al. | |
| 2015/0128971 A1* | 5/2015 | Verleur | H02J 7/00 131/329 |
| 2015/0216823 A1 | 8/2015 | Chatterjee | |
| 2015/0258178 A1 | 9/2015 | Gong | |
| 2016/0058960 A1* | 3/2016 | Papania | A61M 15/0063 600/103 |
| 2016/0101245 A1* | 4/2016 | Hoekman | A61M 15/0028 128/200.23 |
| 2016/0228433 A1 | 8/2016 | Haruta et al. | |

FOREIGN PATENT DOCUMENTS

| | | |
|---|---|---|
| EP | 1165044 A2 | 1/2002 |
| GB | 806284 A | 12/1958 |
| GB | 1517642 A | 7/1978 |
| JP | H08322934 A | 12/1996 |
| JP | 2016520378 A | 7/2016 |
| WO | WO 1986001731 A1 | 3/1986 |
| WO | WO 1999013930 A1 | 3/1999 |
| WO | WO 2000054887 A1 | 9/2000 |
| WO | WO 2001036033 A2 | 5/2001 |
| WO | WO 2002009707 A1 | 2/2002 |
| WO | WO 2007012853 A1 | 2/2007 |
| WO | WO 2008059385 A2 | 5/2008 |
| WO | WO-2017/044897 A1 | 3/2017 |

OTHER PUBLICATIONS

Baron, "Orally Inhaled Dihydroergotamine; Reviving and Improving a Classic", Future Neurology, May 2011, 11 pages.
Constantino, et al., "Intranasal administration of acetylcholinesterase inhibitors", BMC Neuroscience, Dec. 10, 2008, 3 pages.
EP Office Action for 14727320.5, dated Nov. 9, 2016, 6 pages.
EP Search Report for 09707800.0 dated Jul. 1, 2015, 12 pages.
EP Search Report for 11818832.5 dated Sep. 24, 2014, 6 pages.
Hanson, et al., "Intranasal delivery of growth differentiation factor 5 to the central nervous system", Drug Delivery, 19(3):149-54, Feb. 2012, 7 pages.
Hoekman, J.D., "The Impact of Enhanced Olfactory Deposition and Retention on Direct Nose-to-Brain Drug Delivery", UMI Dissertation Publishing, Apr. 11, 2011, 181 pages.
International Search Report for PCT/US/2009/033468 dated Dec. 2, 2009, 5 pages.
Kumar, et al., "Nasal Drug Delivery: A Potential Route for Brain Targeting" The Pharma Innovation Journal, vol. 2, No. 1, Mar. 2013. 9 pages.
Ozsoy, et al., "Nasal Delivery of High Molecular Weight Drugs", Molecules Journal, Sep. 23, 2009, 26 pages.
Parvathi, "Intranasal Drug Delivery to Brain: An Overview," published in the International Journal of Research in Pharmacy and Chemistry 2012, 2(3), 7 pages.
PCT International Search Report and Written Opinion, PCT Application No. PCT/US2018/62296, dated Mar. 11, 2019, 15 pages.
Renner, et al., "Intranasal delivery of growth differentiation factor 5 to the central nervous system," Drug Delivery, Feb. 2012, 7 pages.
Stevens, et al., "Systemic and Direct Nose-to-Brain Transport Pharmacokinetic Model for Remoxipride after Intravenous and Intranasal Administration", in "Drug Metabolism and Disposition", The American Society for Pharmacology and Experimental Therapeutics, 2011, vol. 39, No. 12, 8 pages.
Talegaonkar, et al., "Intranasal delivery: an approach to bypass the blook brain barrier", Indian J Pharmacol, Jun. 2004, vol. 36, Issue 3, 8 pages.
The PCT Search Report and Written Opinion dated Mar. 27, 2012 for PCT application No. PCT/US2011/048435, 14 pages.
Westin et al., "Direct Nose to Brain Transfer of Morphine After Nasal Administration to Rats", Pharmaceutical Research, vol. 23, No. 3, Mar. 2006, 8 pgs.
Westin, "Olfactory Transfer of Analgesic Drugs After Nasal Administration", Digital Comprehensive Summaries of Uppsala Dissertations from the Faculty of Pharmacy 55, May 11, 2007, 66 pages.
Yamada, et al., "Nose-to-brain delivery of TS-002, prostaglandin D2 analogue", Journal of Drug Targeting, Jan. 2007, 9 pages.
Yimam, et al., "Effects of lipid association on lomustine (CCNU) administered intracerebrally to syngeneic 36B-10 rat brain tumors", Cancer Letters 244(2), Dec. 2006, 9 pages.
Ying, "The nose may help the brain: intranasal drug delivery for treating neurological diseases" Future Medicine, 3(1), Jan. 2008, 4 pages.
Zhang, et al., "The brain targeting efficiency following nasally applied MPEG-PLA nanoparticles in rats", Journal of Drug Targeting, Jun. 2006, 11 pages.
The Japan Patent Office, Notice of Rejection, Japanese Patent Application No. 2020-528005, dated Apr. 26, 2022, 11 pages.

* cited by examiner

Shuttle
305

Compound Container
340

Dip Tube
310

Collar
320

Propellant Canister
110

INTRANASAL DEVICE WITH DIP TUBE

CROSS-REFERENCE TO RELATED APPLICATION

This application claims the benefit of U.S. Provisional Application No. 62/589,306, filed on Nov. 21, 2017, which is herein incorporated by reference in its entirety.

BACKGROUND

Depositing drug on the olfactory region of the nasal cavity is difficult to accomplish due to the complex architecture of the nasal cavity and the turbinate guided air path for inhaled breath through the nose. These natural structures act to prevent materials from depositing on the olfactory region as a way to protect this entry way into the central nervous system (CNS). Existing nasal drop or spray devices are designed to saturate the lower nasal cavity. Drug deposited on the lower nasal cavity is absorbed into the blood stream instead of the CNS, eliminating an advantage of using the nasal route for CNS delivery.

A more elegant approach to the intranasal delivery of compounds or mixtures is needed.

SUMMARY

A device for delivering a compound to the olfactory region of the nasal cavity is described. In one embodiment, the device includes an actuator body and a tip configured to removably couple to the actuator body. The actuator body comprises a propellant channel that is configured to be in fluid communication with a canister containing a propellant. The tip comprises a tip stem, a dip tube, a delivery channel, one or more puncture members, and an outlet orifice. The tip stem comprises a cavity and an opening such that the cavity is in fluid communication with the propellant channel, where the cavity is configured to receive a compound container containing the compound and where the compound container is configured to move between a sealed state and an unsealed state within the cavity. The dip tube is positioned within the cavity, and the dip tube comprises the delivery channel that extends from a proximal end to a distal end of the dip tube. The one or more puncture members are each configured to puncture the compound container when the shuttle is in the unsealed state such that the punctured compound container is in fluid communication with the propellant channel and the delivery channel. The outlet orifice is in fluid communication with the delivery channel, such that propellant released from the canister travels through the propellant channel and into the cavity, through the plurality of openings and into the compound container, thereby contacting the compound and propelling the compound through the delivery channel and out the outlet orifice.

In one embodiment, at least one puncture member is disposed at a distal end of the dip tube. In one embodiment, the device further comprises a collar that includes one or more of the puncture members, where the collar includes one or more bypass openings that are in fluid communication with the propellant channel such that released propellant is introduced into the compound container. In one embodiment, the puncture member(s) of the dip tube puncture the compound container first, and the puncture member(s) of the collar puncture the compound container second.

The invention will best be understood by reference to the following detailed description of various embodiments, taken in conjunction with any accompanying drawings. The discussion below is descriptive, illustrative and exemplary and is not to be taken as limiting the scope defined by any appended claims.

The figures depict embodiments of the present disclosure for purposes of illustration only. One skilled in the art will readily recognize from the following description that alternative embodiments of the structures and methods illustrated herein may be employed without departing from the principles, or benefits touted, of the disclosure described herein.

DETAILED DESCRIPTION

Unless stated otherwise, the following terms and phrases as used herein are intended to have the following meanings:

When trade names are used herein, applicants intend to independently include the trade name product formulation, the generic drug, and the active pharmaceutical ingredient(s) of the trade name product.

For clarity of disclosure, and not by way of limitation, the detailed description of the invention is divided into the subsections which follow.

Unless defined otherwise, all technical and scientific terms used herein have the same meaning as commonly understood by one of ordinary skill in the art pertinent to the methods and compositions described. The following references provide one of skill with a non-exclusive guide to a general definition of many of the terms used herein: Hale & Margham, The Harper Collins Dictionary of Biology (Harper Perennial, New York, N.Y., 1991); King & Stansfield, A Dictionary of Genetics (Oxford University Press, 4th ed. 1990); Hawley's Condensed Chemical Dictionary (John Wiley & Sons, 13th ed. 1997); and Stedmans' Medical Dictionary (Lippincott Williams & Wilkins, 27th ed. 2000). As used herein, the following terms and phrases have the meanings ascribed to them unless specified otherwise.

Figure 1:
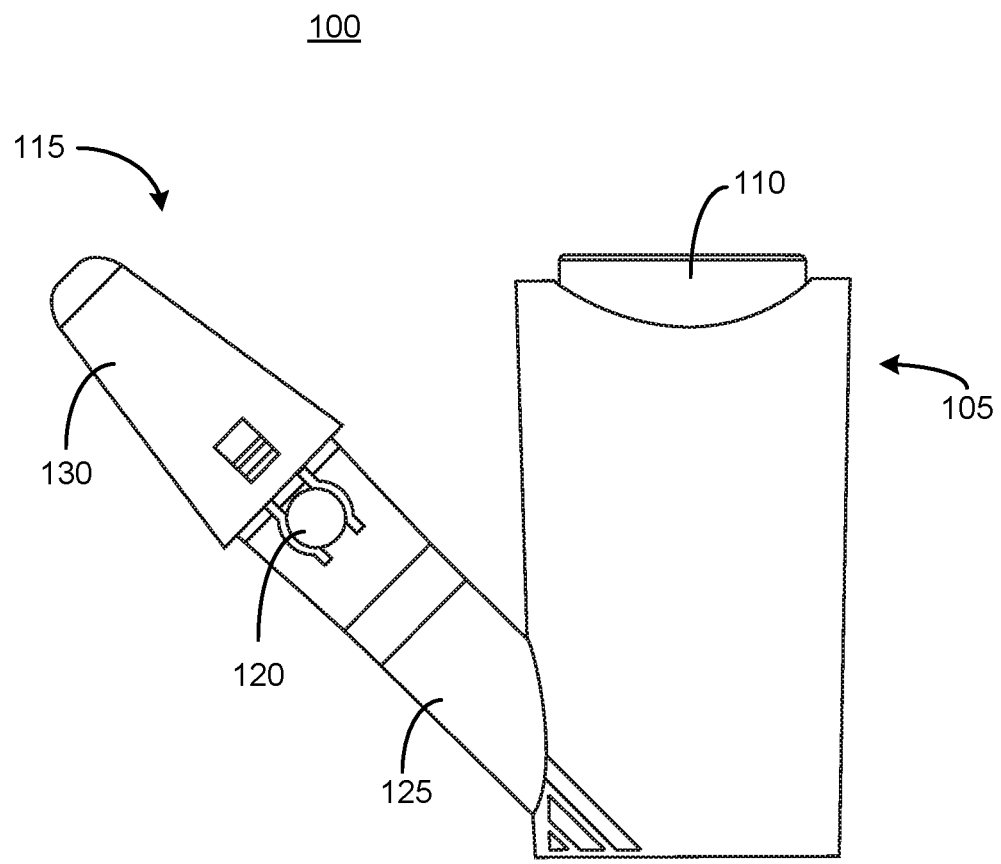
FIG. 1 illustrates an intranasal drug delivery device, in accordance with one or more embodiments.

FIG. 1 illustrates an intranasal drug delivery device 100, in accordance with one or more embodiments. The device 100 is designed to deliver a consistent mass of compound into the nasal cavity. For example, but not limited to, the compound may be an intranasal formulation in a liquid or suspension form. The device 100 targets a specific region of the nasal cavity utilizing a narrow, targeted delivery plume. Specifically, the device 100 provides the compound to the upper one third of the nasal cavity. In one embodiment, the device 100 is used to administer the compound into the olfactory region of a human. The device 100 is designed to receive a compound container containing the compound. The device 100 may be re-used to administer several doses of the compound. In the embodiment of FIG. 1, the device 100 includes an actuator body 105, a propellant canister 110, a tip 115, and a release button 120.

The actuator body 105 is designed to be held in a hand of a user for administering the compound to an olfactory region of the user. In the embodiment of FIG. 1, the actuator body 105 comprises a cavity for receiving the canister 110 and a neck 125 for receiving the tip 115. The actuator body 105 comprises a propellant channel (not shown) having a first end that couples to the canister 110 and a second end that couples to the tip 115 such that the tip 115 is in fluid communication with the canister 110. In the embodiment of FIG. 1, the neck 125 comprises the release button 120, which enables the tip 115 to be coupled and decoupled to the actuator body 105. As shown in FIG. 1, the tip 115 is inserted into the neck 125, while in other embodiments, the neck 125 may be inserted into the tip 115. In some embodiments, the neck 125 and/or the tip 115 may include a sealing interface that creates an airtight seal between the propellant channel and the tip 115 such that propellant released from the canister 110 does not escape out of the propellant channel and is directed into the tip 115.

As shown in FIG. 1, the propellant canister 110 is positioned within the actuator body 105. The propellant canister 110 contains propellant. In one embodiment, the propellant may be pressurized. The propellant is a fluid, for example, a liquid or gas. In one aspect, the propellant is a liquid. In another aspect, the propellant is a gas. Propellants include pharmaceutically suitable propellants. Some examples of pharmaceutically suitable propellants include hydrofluoroalkane (HFA) including but not limited to HFA, HFA 227, HFA 134*a*, HFA-FP, HFA-BP and the like HFA's. In one aspect, the propellant is liquid HFA. In another aspect, the propellant is gaseous HFA. Additional examples of suitable propellants include nitrogen or chloroflourocarbons (CFC). Additionally, propellants may be pressurized air (e.g. ambient air). The canister 110 may be a metered dose inhaler (MDI) device that includes a pressurized canister and metering valve (including stem) (shown in FIG. 11) to meter the propellant upon actuation. In one embodiment, a pump fitment (not shown) secures the metering valve to the canister 110 and holds both components in place during device 100 use. One series of embodiments of the pump fitment consists of securing interfaces that retain the pump fitment within the actuator body 105, provide vertical displacement, and prevent rotation during installation of the canister 110.

The propellant canister 110 may have a capacity for distributing propellant for a certain number of doses. In one embodiment, the device 100 may be shipped without a canister 110 and the canister 110 may be loaded into the actuator body 105 by the user. In some embodiments, the canister 110 may be replaced with a new propellant canister, such that the device 100 may be reused. In one aspect, when the MDI device is actuated, a discrete amount of pressurized HFA fluid is released. The MDI may contain between about 30 to about 300 actuations, inclusive of endpoints, of HFA propellant. The amount of fluid propellant released upon actuation may be between about 20 µl and about 200 µl inclusive of endpoints, of liquid propellant.

The tip 115 delivers the compound to the olfactory region of the user. In the embodiment of FIG. 1, the tip 115 includes a tip stem (shown in FIG. 2A) and a tip cone 130. The tip 115 may be coupled and decoupled to the actuator body 105 by inserting the tip stem into the neck 125 of the actuator body 105, which enables a user to load and unload a compound container into and from the tip 115. In some embodiments, the compound container may be inserted into a shuttle (shown in FIG. 6) that is inserted into the tip 115. The shuttle may protect the compound container, which may be, for example, a liquid dose capsule. The tip cone 130 is positioned within a nostril of the user for aiming the delivery of the compound to the olfactory region. The tip 115 is discussed in further detail with regard to FIGS. 2A-2B.

Figure 2A:
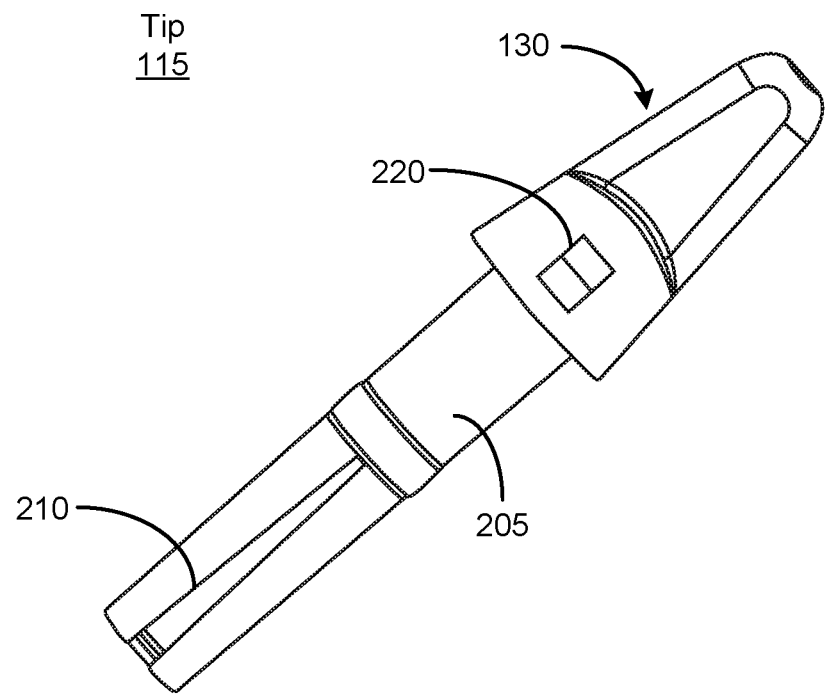
FIGS. 2A and 2B illustrate a tip of the device and a tip cone, in accordance with one or more embodiments.
Figure 2B:
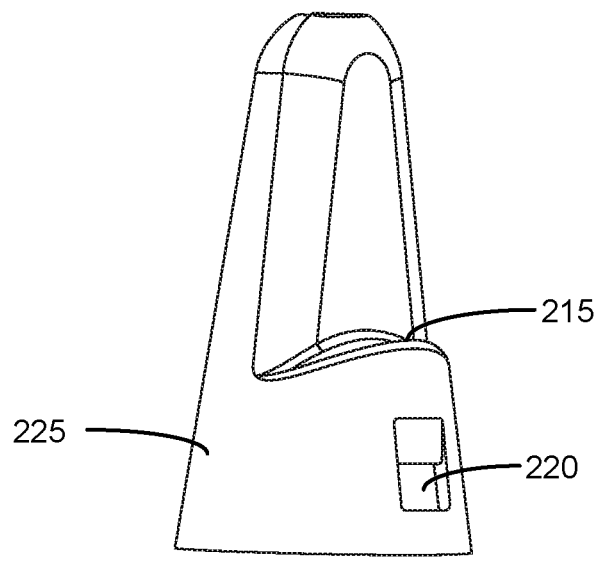
Figure 4:
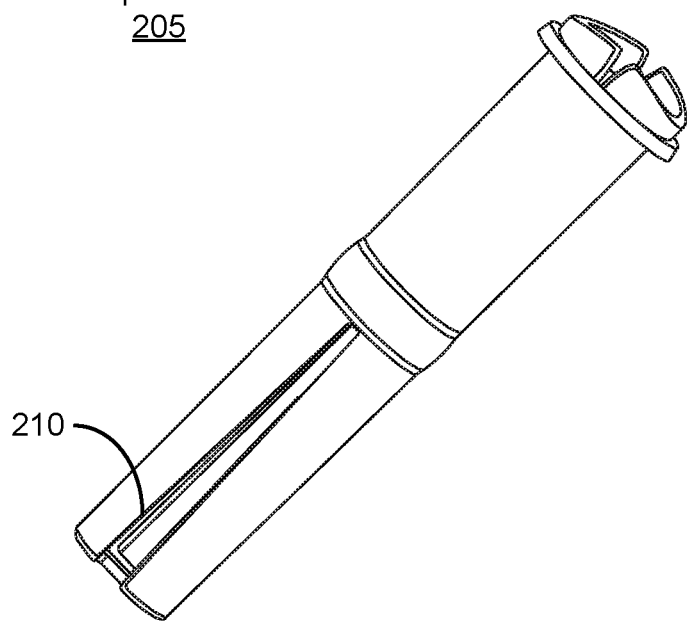
FIG. 4 illustrates a tip stem, in accordance with one or more embodiments.

FIGS. 2A and 2B illustrate the tip 115 of the device and the tip cone 130, in accordance with one or more embodiments. In the embodiments of FIGS. 2A-2B, the tip 115 includes the tip cone 130 and the tip stem 205. The tip cone 130 and the tip stem 205 may be coupled and decoupled from each other for loading and unloading a compound container into and from the tip stem 205. As shown in FIG. 2A, the tip stem 205 is the first half of the tip 115 body. The tip stem 205 seals on the proximal end to the tip cone 130 during assembly. The tip stem 205 is installed into the actuator neck 125 and may have a tapered cylindrical face for inserting into the actuator 125. A seal is formed between the external surface of the tip stem 205 and an internal surface of the actuator neck 125, allowing the tip 115 to become pressurized. The seal may be formed by a sealing interface, an interference fit, or some combination thereof. In the embodiment of FIG. 2A, the tip stem 205 includes one or more slots 210 on a tapered surface of the tip stem 205, also shown in FIG. 4. The slots 210 are designed to interface with ribs on the internal surface of the actuator neck 125. The slots may ensure proper rotational alignment of the tip 115 relative to the actuator body 105. In this configuration, inserting the tip 115 into the actuator neck 125 also causes the ribs to drive a shuttle (not shown) housed within the tip stem 205 forward towards the tip cone 130. The slots 210 are also in fluid communication with the propellant channel such that released propellant travels into the tip stem 205.

As shown in FIG. 2B, the tip cone 130 is the second half of the tip 115 body. The larger end of the tip cone 130 is joined and sealed to the tip stem 205. The tip cone 130 is designed to receive a dip tube, a collar, and a nozzle, which will be discussed in regard to FIGS. 3A and 3B. The external geometries of the tip cone 130 provide proper alignment of the tip 115 during insertion into the nostril of the user. In one example, a flat side of the tip 115 (not shown) lies parallel to and against the septum, with a depth stop guard 215 providing correct depth of insertion. The tip 115 can be installed in either a left or right orientation on the actuator neck 125, allowing dosing into both sides of the nose with the same tip design. One or more side openings 220 on a skirt 225 of the tip cone 130 receive reciprocal clip features of the actuator neck 125. Drafted faces on the tip cone 130 lead the clip features towards the side openings 220, which keeps installation forces low, while the clip features having a ledge in a removal direction of the tip 115 restricts the tip 115 from ejecting during use. The clip features also provide the user tactile feedback to confirm the tip 115 is fully installed. The clip features of the actuator neck 125 are coupled or directly connected to the release button 120 such that the tip 115 may be decoupled from the actuator neck 125 upon actuation of the release button 120.

Figure 3A:
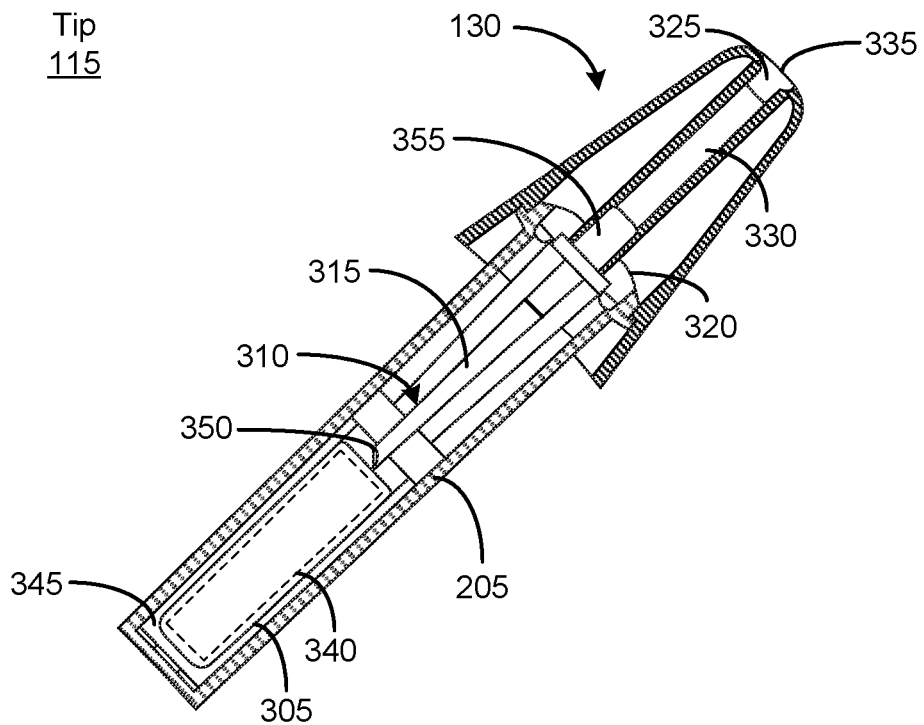
FIGS. 3A and 3B illustrate a cross-sectional view of the tip, in accordance with one or more embodiments.
Figure 3B:
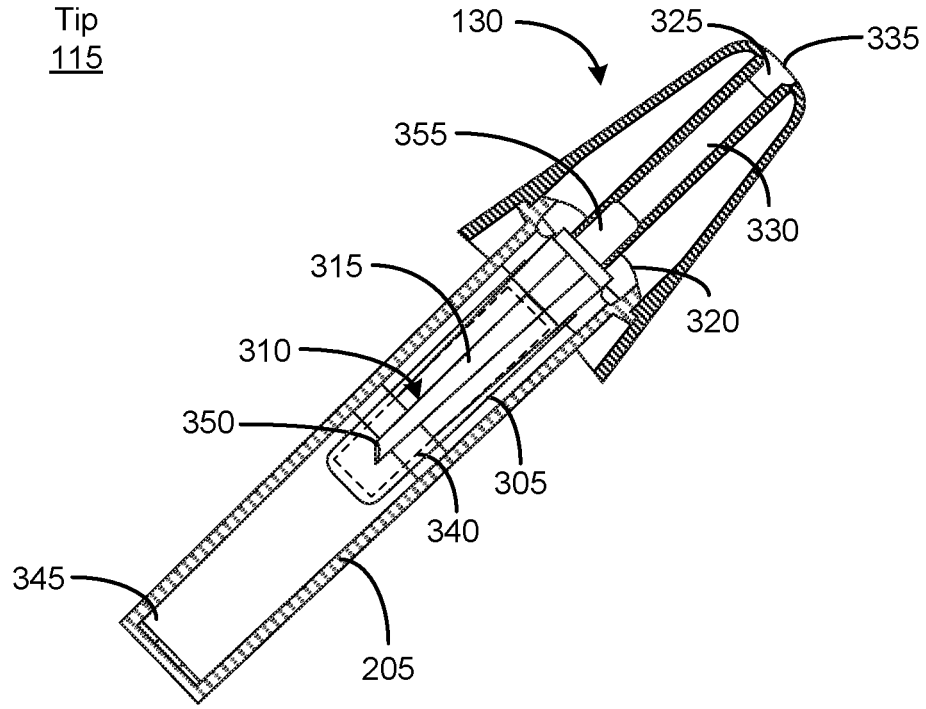

FIGS. 3A and 3B illustrate a cross-sectional view of the tip 115, in accordance with one or more embodiments. In the embodiments of FIGS. 3A and 3B, the tip 115 includes the tip cone 130, the tip stem 205, a shuttle 305, a dip tube 310, a delivery channel 315, a collar 320, a nozzle 325, a nozzle channel 330, and an outlet orifice 335. In use, the shuttle 305 houses a compound container 340 containing the compound and moves between a sealed state (shown in FIG. 3A), where the compound container 340 is sealed, and an unsealed state (shown in FIG. 3B), where the compound container 340 has been punctured by the dip tube 310 and the collar 320. The dip tube 310 includes a puncture member 350 that punctures the compound container 340 such that the compound container 340 is in fluid communication with the delivery channel 315, which is in fluid communication with the nozzle channel 330, the nozzle 325, and the outlet orifice 335. The collar 320 includes a puncture member (not shown) that punctures the compound container 340 such that the compound container is in fluid communication with the propellant channel, such that propellant released from the canister 110 travels through the propellant channel and into the compound container 340, thereby contacting the compound and propelling the compound through the delivery channel 315 and the nozzle 325 and out the outlet orifice 335.

The shuttle 305 receives the compound container containing the compound. In some embodiments, the compound container may be a blow fill sealed (BFS) ampoule. In one example, the BFS ampoule is a polyethylene liquid dose capsule, and in other embodiments, the ampoule may be composed of other types of suitable plastic. A film is blow molded into a defined geometry, filled with a designated liquid dose, and sealed. The ampoule provides a liquid and vapor barrier for the intranasal formulation within. The BFS ampoule containing the liquid dose, also shown in FIG. 6, is installed into the shuttle 305, also shown in FIG. 5, which is in turn installed into the tip stem 205. FIG. 3A illustrates the shuttle 305 positioned within a cavity 345 of the tip stem 205 in the sealed state, where the shuttle 305 is at a distal end of the cavity 345 and the compound container 340 is sealed. FIG. 3B illustrates the shuttle 305 positioned within the cavity 345 of the tip stem 205 in the unsealed state, where the shuttle 305 is at a proximal end of the cavity 345 and the compound container 340 has been punctured by the puncture member 350 of the dip tube 310 and the puncture member(s) of the collar 320. Inserting the tip 115 into the actuator neck 125 causes ribs on the internal surface of the actuator neck 125 to drive the shuttle 305 forward towards the tip cone 130, moving the shuttle 305 from the sealed state to the unsealed state. In the unsealed state, the shuttle and the BFS ampoule are punctured by the puncture member 350 of the dip tube 310 and the puncture member(s) of the collar 320, thereby breaking the seal of the BFS ampoule and providing a flow path for the liquid dose to be evacuated from the BFS ampoule.

Figure 5:
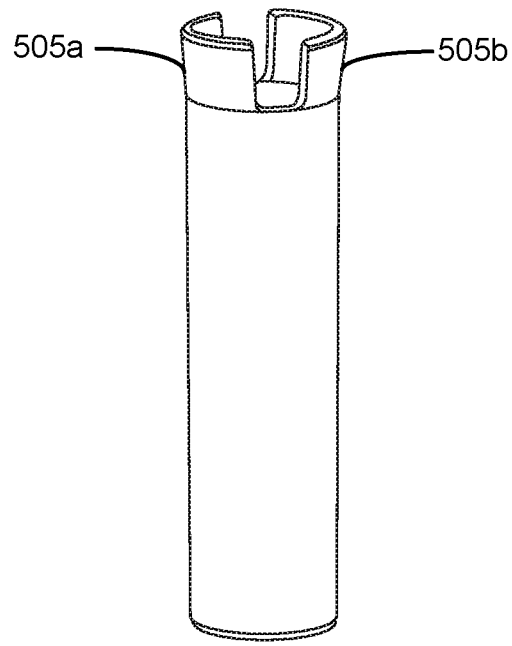
FIG. 5 illustrates a shuttle, in accordance with one or more embodiments.
Figure 6:
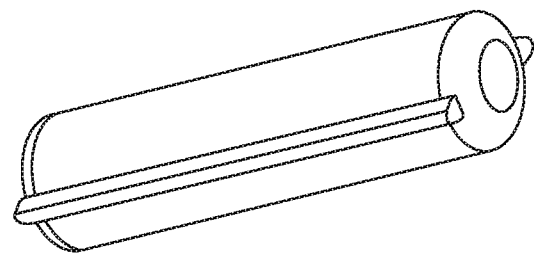
FIG. 6 illustrates a compound container, in accordance with one or more embodiments.

Referring to FIG. 5, an outer surface of the shuttle 305 rides on ribs on an internal surface of the tip stem 205. The shuttle 305 provides a rigid body for the ribs on the internal surface of the actuator neck 125 to press against to propel the shuttle 305 forward towards the proximal end of the tip 115, rather than pushing directly onto the flexible BFS ampoule itself. The shuttle 305 may have internal support features (e.g., ribs, notches, or the like) (not shown) to support the BFS ampoule, in one example concentrically, so that the BFS ampoule may be punctured. The splayed lips on the proximal end of the shuttle 305 prevent the shuttle 305 from being inserted backwards into the tip stem 205. Additionally, the splayed lips 505 ensure that the shuttle 305 and the tip stem 205 will be in interference across tolerance ranges. The shuttle 305 also shields the dose containing BFS ampoule from sight, limiting light exposure, device tampering, or premature ampoule puncture from external objects.

Figure 7:
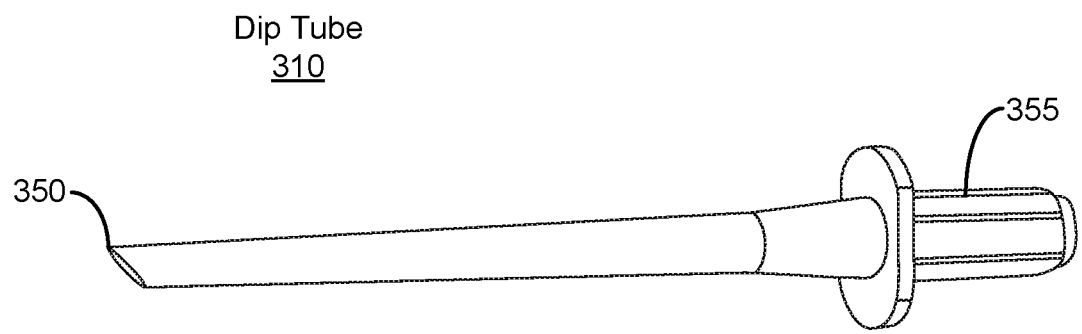
FIG. 7 illustrates a dip tube, in accordance with one or more embodiments.

Referring back to FIG. 3, the dip tube 310 is positioned within the cavity 345 of the tip stem 205. The dip tube 310, also shown in FIG. 7, includes a delivery channel 315 that extends from a proximal end to a distal end of the dip tube 310. The delivery channel 315 is in fluid communication with the nozzle channel 330, the nozzle 325, and the outlet orifice 335. In the embodiment of FIG. 3, the dip tube 310 includes a puncture member 350 about the distal end of the dip tube 310. In the embodiment of FIG. 3, the puncture member 350 is an angled edge about the distal end of the dip tube 310. In other embodiments, the dip tube 310 may include more than one puncture member at the distal end, and the shape and/or angle of the puncture member may vary. The puncture member 350 punctures the compound container 340 as the shuttle 305 is driven towards the nose cone 130 from the sealed state to the unsealed state by the ribs on the internal surface of the actuator neck 125. In this configuration, the dip tube punctures through the compound container 340 and seats inside the compound container 340 (e.g., near the base of the compound container 340). In one embodiment, the dip tube 310 may have external walls that taper such that the punctured hole in the compound container 340 created by the puncture member 350 is smaller than the diameter of the dip tube 310, thereby creating a water and gas-tight seal between the dip tube 310 and the compound container 340. The tapered walls may also increase the rigidity of the puncture member 350. A protruding ring feature 355 on the proximal end of the dip tube 310 provides a mating interface for mating with the nozzle channel 330. An interference fit between the protruding ring feature 355 of the dip tube 310 and the nozzle channel 330 may seal the components such that the delivery channel 315 and the nozzle channel 330 are in fluid communication.

Figure 8:
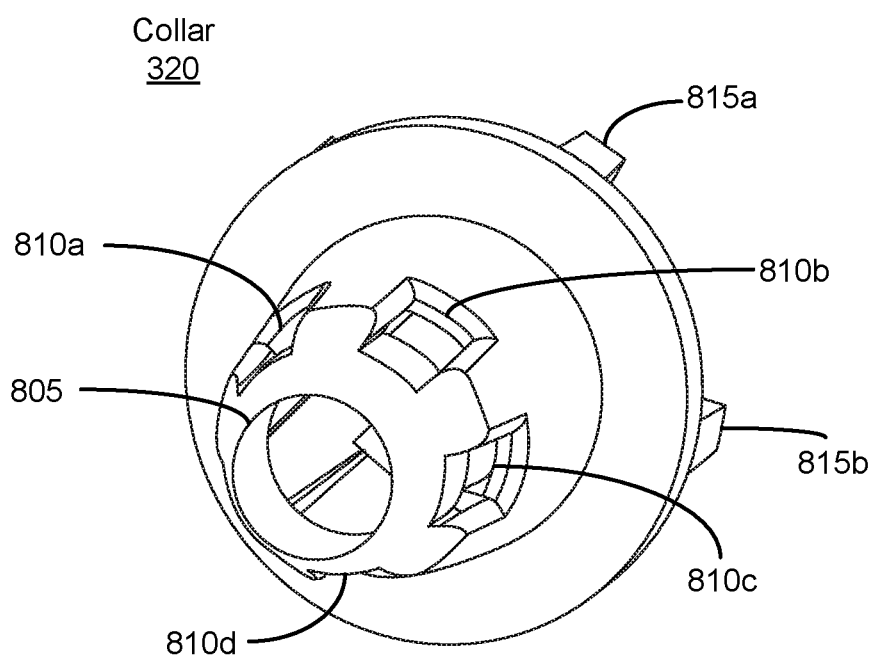
FIG. 8 illustrates a collar, in accordance with one or more embodiments.

The collar 320 is positioned about the proximal end of the dip tube 310 within the tip cone 130. The collar 320 is designed to puncture the compound container 340 to create a flow path between the propellant channel and the compound container 340 such that propellant released from the canister 110 flows into the punctured compound container 340. Referring also to FIG. 8, the collar 320 includes a central opening 805, one or more bypass openings 810, and one or more puncture members 815. The one or more puncture members 815 are on a bottom surface of the collar 320. The collar 320 is installed over the dip tube 310, where the central opening 805 mates with the protruding ring feature 355 of the dip tube 310 and forms a seal to hold the collar in place. The collar 320 is oriented such that the puncture members 815 are oriented towards the compound container 340. During installation of the tip 115 into the actuator neck 125, the compound container 340 is punctured first by the dip tube 310 and second by the collar 320. The collar 320 seats into the top of the compound container 340. The bypass openings 810 around the perimeter of the collar 320 introduce propellant into the compound container during device 100 actuation. Any dose displaced into the collar 320 during puncture of the compound container 340 is forced back into the compound container 340 by the propellant. In this manner, the dose and the propellant are mixed together in the container 340 and then evacuated through the dip tube 310 during device 100 actuation.

Figure 9:
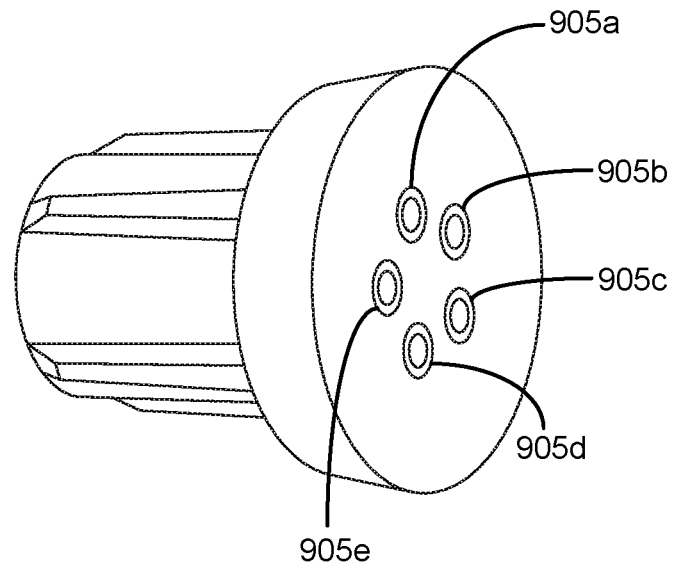
FIG. 9 illustrates a nozzle, in accordance with one or more embodiments.

Referring back to FIG. 3, the nozzle 325 directs the spray of propellant and dose from the nozzle channel 330 and out the outlet orifice 335 such that the spray is targeted towards the olfactory region of a user. The nozzle 325 may form a narrow plume. The nozzle 325 is positioned within the nozzle channel 330 of the tip cone 130. In the embodiment of FIG. 3, the nozzle 325 is at the proximal end of the tip cone 130, adjacent to the outlet orifice 335. Referring also to FIG. 9, the nozzle 325 may include one or more channels 905 that may be oriented parallel to a central axis of the nozzle 325 or tapered towards or away from the central axis. The nozzle channel 330 connecting the nozzle 325 and the dip tube 310 may serve as a displacement volume for the liquid dose during puncture of the compound container. The nozzle 325 forms a liquid and gas-tight seal around the outer diameter within the nozzle channel 330. During actuation, propellant evacuates liquid dose from the compound container 340, pushing it through the nozzle channel 330 and out the nozzle 325. In some embodiments, the type of nozzle 325 installed into the nozzle channel 330 may vary, which enables the device 100 to adapt to different formulation types or plume styles.

Figure 10:
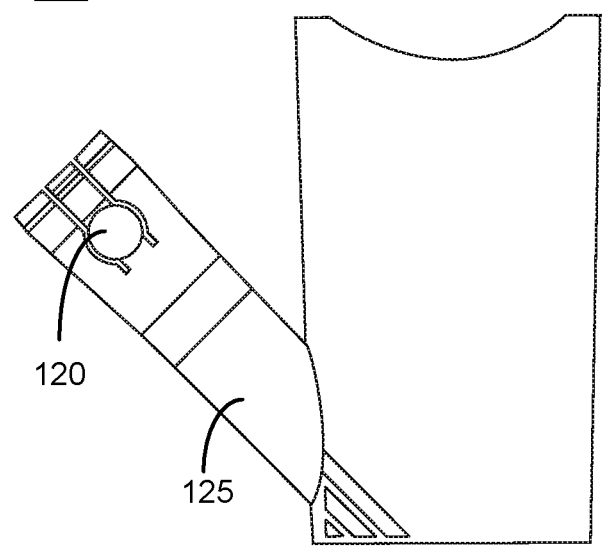
FIG. 10 illustrates an actuator body, in accordance with one or more embodiments.
Figure 11:
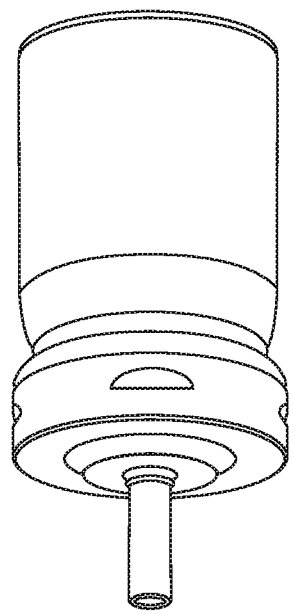
FIG. 11 illustrates a canister containing a propellant, in accordance with one or more embodiments.

The actuator body 105, shown in FIGS. 1 and 10, couples the propellant canister 110, shown in FIGS. 1 and 11, to the tip 115. The propellant canister 110 seats and seals inside a large upright cavity of the actuator body 105. During use, the tip 115 is inserted into the neck 125 of the actuator body 105. Internal ribs (not shown) on the internal surface of the actuator neck 125 contact the compound container 340 and drive the compound container 340 towards the puncture members on the dip tube 310 and the collar 320. The actuator neck 125 seals to the tip 115 to pressurize the tip 115. In one example, clips near the end of the actuator neck 125 interface with the tip cone during use.

The propellant canister 110 provides the propulsion for the device. The canister 110 is inserted into the actuator body 105. During use, the canister 110 is depressed, releasing a metered volume of liquid propellant. As the propellant vaporizes and expands, the propellant travels through the propellant channel of the actuator body and into the tip stem 205 through the slots 210. Since the tip stem 205 is pressurized, the propellant forces the liquid dose out of the compound container 340 and out through the nozzle 325 and the outlet orifice 335. In one embodiment, the propellant fills the tip stem (e.g., traveling through the cavity 345, through the bypass openings 810, into the nose cone 130), such that the displaced air volume forces the liquid dose out of the compound container 340. In one embodiment, the propellant fills the tip stem 205 and then enters the compound container 340 through the punctured openings, where the propellant and compound mix together before exiting through the outlet orifice 335. The canister 110 may contain enough propellant for multiple doses. Propellant type and volume may be selected by one of skill in the art based on performance data.

Additional Configuration Information

The foregoing description of the embodiments of the disclosure has been presented for the purpose of illustration; it is not intended to be exhaustive or to limit the disclosure to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims.

What is claimed:

1. A device for delivering a compound to an olfactory region of a nasal cavity comprising:
   an actuator body comprising:
      a propellant channel configured to be in fluid communication with a canister containing a propellant;
   a tip configured to removably couple to the actuator body, the tip comprising:
      a tip stem comprising a cavity and an opening such that the cavity is in fluid communication with the propellant channel when the tip is coupled to the actuator body, wherein the cavity is configured to receive a sealed compound container containing the compound;
      a dip tube positioned within the cavity, the dip tube comprising a delivery channel that extends from a proximal end to a distal end of the dip tube;
      one or more puncture members that are each configured to puncture the compound container such that the punctured compound container is in fluid communication with the propellant channel and the delivery channel;
      an outlet orifice located at a proximal end of the device, the outlet orifice in fluid communication with the delivery channel from the proximal end of the dip tube, such that, when the tip is coupled to the actuator body and the compound container in the cavity is unsealed, propellant released from the canister can travel through the propellant channel and into the cavity, and into the compound container, thereby contacting the compound and propelling the compound through the delivery channel and out the outlet orifice; and
      a collar positioned at the proximal end of the dip tube within the tip, the collar comprising one or more bypass openings, wherein the one or more bypass openings are in fluid communication with the propellant channel such that released propellant is introduced into the compound container,
      wherein the opening of the tip stem is configured to interface with an internal surface of the actuator body.

2. The device of claim 1, wherein at least one of the one or more puncture members is disposed at the proximal end of the dip tube.

3. The device of claim 1, wherein the collar couples about a portion of the dip tube, and at least one of the one or more puncture members is positioned on the collar.

4. The device of claim 3, wherein at least one of the one or more puncture members is disposed at the proximal end of the dip tube, and the at least one of the one or more puncture members disposed at the proximal end of the dip tube is configured to puncture the compound container first and the at least one of the one or more puncture members positioned on the collar is configured to puncture the compound container second when the compound container is in the unsealed state.

5. The device of claim 1, further comprising a tip cone configured to couple to the tip stem, wherein the tip cone is configured to align the device with a nostril of a user.

6. The device of claim 5, wherein the tip cone comprises a depth stop guard that is configured to indicate an amount of depth insertion into the nostril of the user.

7. The device of claim 1, further comprising a nozzle in fluid communication with the delivery channel and the outlet orifice, wherein the nozzle comprises one or more channels.

8. The device of claim 1, further comprising a sealing interface between the tip and the actuator body.

9. The device of claim 1, wherein the compound container is composed of a plastic film.

10. The device of claim 1, wherein the actuator body comprises a release button that, when actuated, is configured to decouple the tip from the actuator body.

11. The device of claim 10, wherein the release button is connected to one or more clip features that are configured to mate with one or more openings on the tip, thereby coupling the tip to the actuator body.

12. The device of claim 1, further comprising a shuttle configured to house the compound container, wherein the shuttle is configured to be inserted into the cavity.

13. The device of claim 12, wherein the shuttle is configured to provide a rigid body for moving the compound container between a sealed state and an unsealed state.

14. The device of claim 12, wherein the shuttle comprises one or more splayed lips that are configured to indicate an orientation of the shuttle upon insertion into the cavity.

15. The device of claim 1, wherein the device is configured to deliver a liquid compound.

16. The device of claim 1, wherein the collar comprises a central opening surrounded by the one or more bypass openings, and the central opening is configured to fit the dip tube.

\* \* \* \* \*